United States Patent [19]
Kühn et al.

[11] Patent Number: 5,316,648
[45] Date of Patent: May 31, 1994

[54] ELECTROCHEMICAL MEASURING CELL FOR DETECTING GASES AND VAPORS

[75] Inventors: Uwe Kühn, Wesenberg; Herbert Kiesele; Stephan Haupt, both of Lübeck, all of Fed. Rep. of Germany

[73] Assignee: Drägerwerk Aktiengesellschaft, Lübeck, Fed. Rep. of Germany

[21] Appl. No.: 943,678

[22] Filed: Sep. 11, 1992

[30] Foreign Application Priority Data

Sep. 14, 1991 [DE] Fed. Rep. of Germany ....... 4130690
Oct. 12, 1991 [DE] Fed. Rep. of Germany ....... 4133831

[51] Int. Cl.[5] .......................................... G01N 27/26
[52] U.S. Cl. ................................. 204/415; 204/412; 204/416; 204/418; 204/419; 204/290 R; 204/283
[58] Field of Search ............... 204/412, 415, 416, 419, 204/432, 153.13, 153.17, 153.19, 290 R, 283, 418

[56] References Cited

U.S. PATENT DOCUMENTS

| | | | |
|---|---|---|---|
| 3,124,520 | 3/1964 | Juda | 204/283 |
| 3,239,444 | 3/1966 | Heldenbrand | 204/415 |
| 4,961,834 | 10/1990 | Kühn et al. | 204/412 |
| 5,041,204 | 8/1991 | Kühn et al. | 204/415 |
| 5,084,144 | 1/1992 | Reddy et al. | 204/290 R |
| 5,133,842 | 7/1992 | Taylor et al. | 204/290 R |

FOREIGN PATENT DOCUMENTS 2627271 12/1977 Fed. Rep. of Germany.

*Primary Examiner*—John Niebling
*Assistant Examiner*—Bruce F. Bell
*Attorney, Agent, or Firm*—Walter Ottesen

[57] ABSTRACT

An electrochemical measuring cell has a three-electrode system including electrode, counter electrode and reference electrode in an electrolyte. The measuring cell has an additive promoting the electrochemical reaction and is selective and highly sensitive for the detection of hydrogen halides and also provides a stable measuring signal. A measuring cell of this kind has an additive of tetrachloroauric acid in the electrolyte for detecting hydrochloric acid with all electrodes being made of gold. The counter electrode is protected by a cation exchange membrane to provide a further improvement.

13 Claims, 2 Drawing Sheets

ELECTROCHEMICAL MEASURING CELL FOR DETECTING GASES AND VAPORS

FIELD OF THE INVENTION

The invention relates to an electrochemical measuring cell for detecting and determining gaseous and vaporous components in a measuring sample. The measuring cell includes a measuring electrode and a counter electrode which are disposed in an electrolyte having an additive which stimulates the electrochemical reaction. The measuring and counter electrodes as well as the electrolyte and additive are accommodated in a measuring chamber which is closed off relative to the ambient by a membrane permeable for the substance to be detected and impermeable to the electrolyte and the additive.

BACKGROUND OF THE INVENTION

Such an electrochemical measuring cell is disclosed in published German patent application 2,627,271. The electrochemical measuring cell disclosed herein includes an ion selective measuring electrode and counter electrode made of silver which are dipped into an electrolyte of sulfuric acid and a silver sulfate as an additive. When detecting hydrochloric acid for example, the chloride ions dissolved in the electrolyte react with the silver ions and form a silver chloride deposit between the measuring electrode and the membrane. This leads to a change or blockage of the diffusion paths during the course of the measuring operation which, in turn, leads to an unwanted falsification of the measuring result. Accordingly, this measuring cell makes the detection possible by means of the additive but the electrode becomes blocked.

In a measuring cell disclosed in U.S. Pat. No. 5,041,204, the gas sample reaches the semipermeable membrane subjected to the ambient whereupon the component to be detected diffuses through the membrane and is dissolved in the electrolyte. The electrochemical reaction takes place at the interface of the electrolyte/measuring electrode surface. The resulting measurement signal is taken off between the measuring electrode and the counter electrode and is a measure for the concentration of the component to be detected. An additive of copper salt is intended to catalyze the oxidation of the substance to be detected (hydrogen cyanide, sulfur dioxide). Although this additive stimulates the reaction, it does not activate the electrode.

SUMMARY OF THE INVENTION

It is an object of the invention to provide an electrochemical measuring cell of the kind referred to above which is so improved that the cell responds selectively with high sensitivity and supplies a stable measuring signal having a low cross sensitivity with respect to other components, such as hydrogen, in the measuring sample containing the gas to be detected. It is a further object of the invention that the electrode surface and especially the surface of the measuring electrode is not affected with respect to its measuring activity during the entire measuring time.

The electrochemical measuring cell of the invention is for detecting and determining gaseous and vaporous component substances in a measuring sample. The measuring cell includes: a housing having an opening directed toward the ambient containing the sample to be detected and defining a measuring chamber; an electrolyte contained in the chamber and including an additive for promoting the electrochemical reaction; a membrane permeable to the component substances and mounted on the housing for closing off the chamber with respect to the ambient; the membrane being impermeable to the electrolyte and the additive; a measuring electrode and a counter electrode disposed in the chamber so as to be in spaced relationship to each other; the measuring electrode being made of a metal $M^o$ or a metal alloy containing the metal $M^o$ as a main constituent; the additive containing metal ions $M^{n+}$ dissolved in the electrolyte; the metal ions $M^{n+}$ being ions of the metal $M^o$; and, the additive being selected to have an oxidation number (n) equal to or greater than 2 and the additive being further selected so as to cause a synproportioning reaction to take place between the metal $M^o$ and the metal ions $M^{n+}$ dissolved in the electrolyte.

According to a feature of the invention, the additive contains metal ions $M^{n+}$ dissolved in the electrolyte of the same metal $M^o$ from which the measuring electrode is composed with respect to its main component and that the oxidation state (n) is greater or equal to the numerical value 2 and is present with such a value (n) that a synproportioning reaction takes place between the metal $M^o$ of the electrode and the dissolved metal ions $M^{n+}$.

An additive is to be selected in dependence upon the metal selected for the measuring electrode. The additive is then so selected that the same metal (present as a salt or bonded in a complex) is present dissolved in the electrolyte with the additive having such a higher-value oxidation number (n) (equal to or greater than 2), that a synproportioning reaction takes place between the metal of the electrode and the dissolved metal ion. The synproportioning reaction proceeds in the usual manner over several individual steps wherein the necessary electron transfer between $M^o$ and $M^{n+}$ takes place. If the measuring electrode is made of copper for example, then the additive copper (II) chloride is selected (n=2). For platinum as the electrode material, hexachloroplatinate having an oxidation number n=4 would be utilized.

The proceeding synproportioning reaction between the neutral metal ion $M^o$ of the measuring electrode and the multiple charged metal ion in solution effects an etching or a constant uncovering of the measuring electrode surface from some kind of deposit inhibiting the reaction at the electrode surface or changes. A metallic pure surface is always available. In this way, its measuring activity is increased which becomes manifest in an improved response performance. The additive in the electrolyte stimulates the reaction and prevents the electrode from becoming blocked.

The measuring electrode can then either be made of pure metal or a metal alloy with the primary component of the metal alloy being viewed as a partner participating in the synproportioning reaction.

If hydrogen halide is to be detected with the measuring cell, then the measuring electrode preferably is made of gold and the additive is a salt of the general form $HAuX_4$ or $AuX_3$ wherein X is one of the elements chlorine or bromine and the concentration thereof is greater than $10^{-5}$M and is preferably $10^{-3}$M.

The selection of chlorine for X is advantageous for the detection of HCl, HBr, HI and $H_2O_2$; the selection of bromine for X is advantageous for the detection of HBr, HI. Tetrachloroauric acid ($HAuCl_4$) has proven especially suitable for the determination of HCl. Here, n=3.

It has been shown that $H_2O_2$ (hydrogen peroxide) can also be detected with the measuring cell. For this purpose, an additive such as $HAuCl_4$ or $AuCl_3$ or a mixture of these two salts can be used. The sensitive detection possibility for $H_2O_2$ is a good example as to how the synproportioning reaction always exposes the measuring electrode surface and prevents an inhibition of the measuring reaction which would otherwise occur.

Such an electrochemical measuring cell is applied in the chemical industry as well as in the semiconductor industry where gaseous components such as hydrochloric acid or hydrogen bromide (or such compounds which develop HCl in humid air such as $BCl_3$, $BBr_3$, $SiH_2Cl_2$ and $SiCl_4$) must be detected in the work environment of workers in the semiconductor industry. The sensor is characterized by long-term stability and high response speed since the surface of the measuring electrode always remains active because of the electrode reactions which take place and its sensitivity does not significantly diminish even for long-term loading of the measuring cell with the gas component to be detected.

The reaction steps which proceed at the measuring electrode during the measurement of hydrogen halides are demonstrated with the example of the detection of hydrochloric acid and tetrachloroauric acid as additive in the following individual reaction steps:

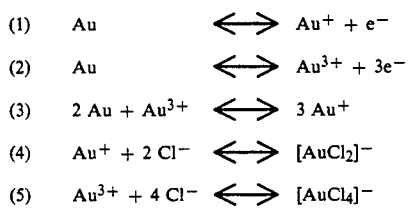

The tetrachloroauric acid dissolved in the electrolyte is in equilibrium with the $Au^{3+}$-ions corresponding to the equations (2) and (3) which is disturbed by the presence of, for example, hydrochloric acid in that the detecting species $Cl^-$ which is considered in this case, disturbs this equilibrium in correspondence to the detection reactions (4) and (5). The chloride ions react with the $Au^+$-ions located on the solid gold electrode surface as well as with the $Au^{3+}$-ions in solution. The $Au^+/Au^{3+}$-ions are removed at the electrode surface by the reaction in accordance with equations (4) and (5) and are resupplied via the decomposition of the electrode. In this way, the electrode surface is continuously renewed and thereby activated. The gold supply is adequate for a continuous operation of the measuring cell for longer than one year.

Because of the addition of tetrachloroauric acid, the measuring electrode surface is continuously renewed during the detection reaction. The measuring cell responds especially well to hydrogen halide and the speed of response is high and the measuring signal remains stable because of the constantly active measuring electrode surface. The same applies to the measurement of $H_2O_2$.

A suitable electrolyte composition for the measurement of HCl comprises an additive of $10^{-1}$ to $10^{-5}$ mol (preferably $10^{-3}$ mol) of tetrachloroauric acid in a 4-mol sulfuric acid. This composition makes possible a continuous measurement to detect hydrogen halides in the ppm-range.

For providing a further long-term stability of the measuring signal, it is advantageous to introduce an additional reference electrode into the electrochemical measuring cell with the reference electrode being made of the same material as the measuring electrode. With the aid of this third electrode, it is possible to fix the reference potential for the work electrode with the aid of a potentiostatic circuit. An electrode potential of 0 volts is possible because of the identical electrode material. This 0 voltage becomes manifest by a short running-in time and a low residual current. In this way, the preconditions are provided for a sensor having a high sensitivity and which is operationally ready very quickly.

During the detection reaction of, for example, hydrochloric acid, an enrichment of the hydrogen halide (hydrochloric acid in the example) takes place at the counter electrode during the reduction of the additive (in the example of tetrachloroauric acid). This enrichment leads to a shift of the reference potential for the measuring electrode which, in turn, leads to a drift of the measuring signal. It is advantageous to protect the counter electrode with a cation exchange membrane in order to prevent this undesired follow-up reaction. In this way, the reduction of the additive such as the tetrachloroauric acid is prevented so that the additive is enriched and an enrichment of the hydrogen halide in the solution no longer takes place.

The use of the ion exchange membrane can take place either in that the membrane is clamped in place in the housing within the electrolyte chamber as a barrier between the measuring electrode and the counter electrode or the surface of the counter electrode is covered with the ion exchange membrane.

A suitable material for the ion exchange membrane is perfluorosulfonated PTFE (Nafion, a trademark of the Dupont company).

BRIEF DESCRIPTION OF THE DRAWING

The invention will now be described with reference to the drawings wherein.

DESCRIPTION OF THE PREFERRED
EMBODIMENTS OF THE INVENTION

Figure 1:
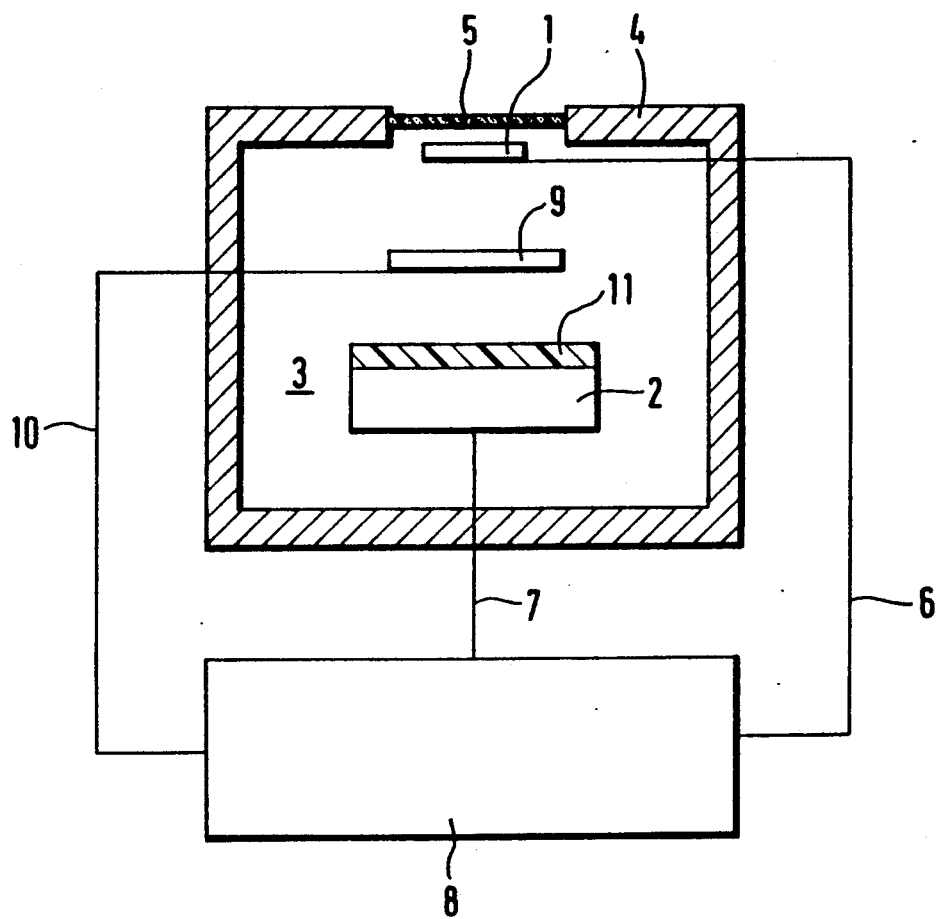
FIG. 1 shows an embodiment of the measuring cell of the invention wherein the counter electrode is covered with an ion exchange membrane; and, FIG. 2 shows another embodiment of the invention wherein the ion exchange membrane is clamped in place in the housing to define a barrier between the measuring electrode and the counter electrode.

FIG. 1 of the drawing shows a measuring cell having a measuring electrode 1, a counter electrode 2 and a reference electrode 9 all made of gold which are disposed in an electrolyte chamber 3 of the measuring cell housing 4. The electrolyte chamber 3 is filled with an aqueous solution of 4-mol sulfuric acid having an additive of $10^{-3}$ mol tetrachloroauric acid. The electrolyte chamber 3 is closed off by a membrane 5 with respect to the ambient which contains the measuring sample containing hydrogen halide. The membrane 5 is permeable to the hydrogen halide.

A covering in the form of an ion exchange membrane 11 is stretched over the counter electrode 2. All electrodes (1, 2, 9) have respective measuring leads (6, 7, 10) which are led through the housing 4 and are connected to an evaluation unit 8 for further processing of the measuring signals. The evaluation unit 8 likewise contains a potentiostatic circuit with the aid of which the reference potential between the reference electrode 9 and the measuring electrode 1 is fixed and maintained.

Figure 2:
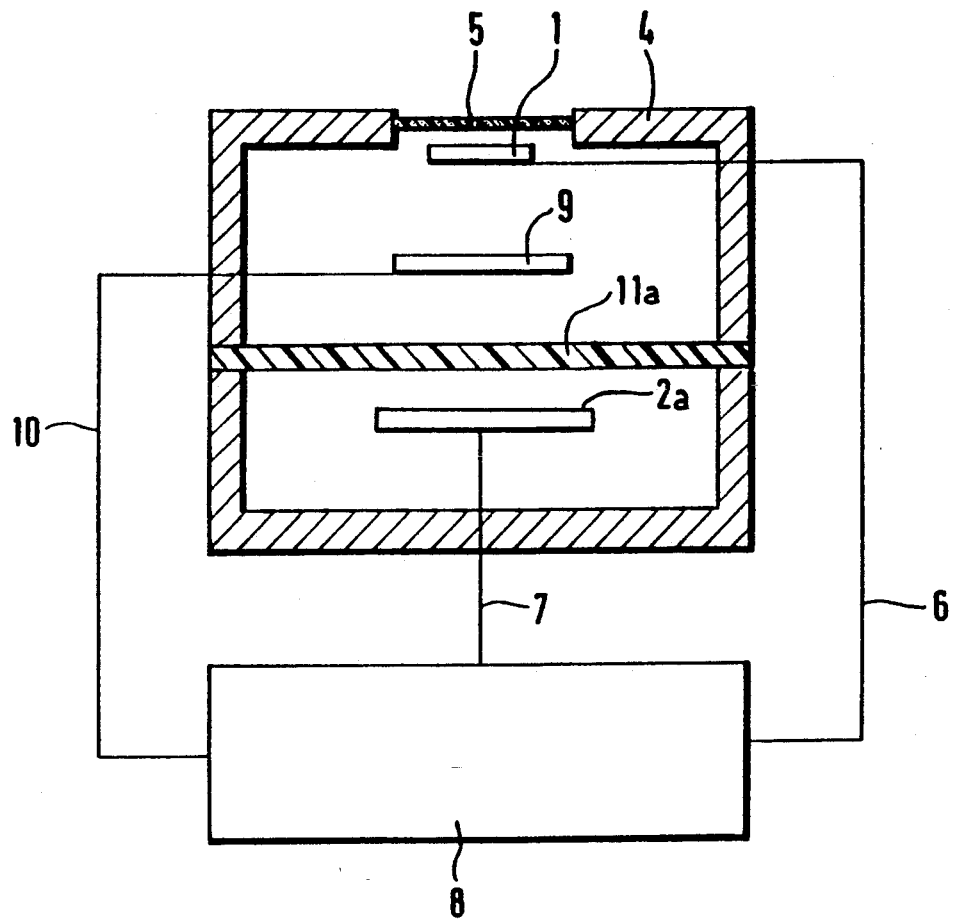

As shown in FIG. 2, the ion exchange membrane 11a can be clamped in place in the housing 4 within the electrolyte chamber 3 as a barrier between the measuring electrode 1 and the counter electrode 2a.

It is understood that the foregoing description is that of the preferred embodiments of the invention and that various changes and modifications may be made thereto without departing from the spirit and scope of the invention as defined in the appended claims.

What is claimed is:

1. An electrochemical measuring cell for detecting and determining gaseous and vaporous component substances in a measuring sample, the measuring cell comprising:
   a housing having an opening directed toward an ambient containing the sample to be detected and defining a measuring chamber;
   an electrolyte contained in said chamber and said electrolyte including an additive for promoting an electrochemical reaction during measurement;
   a membrane permeable to said component substances and mounted on said housing for closing off said chamber with respect to the ambient;
   said membrane being impermeable to the electrolyte and said additive contained therein;
   a measuring electrode and a counter electrode disposed in said chamber so as to be in spaced relationship to each other;
   said measuring electrode being made of metal $M^o$ or a metal alloy containing said metal $M^o$ as a main constituent;
   said additive containing metal ions $M^{n+}$ dissolved in said electrolyte;
   said metal ions $M^{n+}$ being ions of said metal $M^o$; and,
   said additive being selected to have an oxidation number (n) equal to or greater than 2 and said additive being further selected so as to cause a synproportioning reaction to take place between said metal $M^o$ and said metal ions $M^{n+}$ dissolved in said electrolyte.

2. The electrochemical measuring cell of claim 1 for detecting hydrogen halide, said measuring electrode consisting essentially of gold; said additive containing said metal ion in a dissolved form of a salt having the general composition $HAuX_4$ or $AuX_3$ wherein X represents the element Cl or Br.

3. The electrochemical measuring cell of claim 2, said additive being present in said electrolyte in a concentration greater than $10^{-5}$ M.

4. The electrochemical measuring cell of claim 2, said additive being present in said electrolyte in a concentration of $10^{-3}$ M.

5. The electrochemical measuring cell of claim 1 for detecting hydrochloric acid, the measuring cell further comprising an additive of tetrachloroauric acid.

6. The electrochemical measuring cell of claim 1, further comprising a reference electrode made of the same metal or metal alloy as said measuring electrode.

7. The electrochemical measuring cell of claim 1, further comprising an ion exchange membrane for protecting said counter electrode.

8. The electrochemical measuring cell of claim 7, said ion exchange membrane consisting of perfluorosulfonated Poly tetra fluoroethylene.

9. The electrochemical measuring cell of claim 7, said ion exchange membrane being a partition membrane in said measuring chamber and being clamped in said housing so as to be between said measuring electrode and said counter electrode.

10. The electrochemical measuring cell of claim 7, said ion exchange membrane covering the surface of said counter electrode.

11. The electrochemical measuring cell of claim 1 for detecting hydrogen peroxide, said additive being tetrachloroauric acid.

12. The electrochemical measuring cell of claim 1 for detecting hydrogen peroxide, said additive being gold chloride.

13. The electrochemical measuring cell of claim 1 for detecting hydrogen peroxide, said additive comprising a mixture of tetrachloroauric acid and gold chloride.

* * * * *

UNITED STATES PATENT AND TRADEMARK OFFICE
CERTIFICATE OF CORRECTION

PATENT NO. : 5,316,648            Page 1 of 2

DATED : May 31, 1994

INVENTOR(S) : Uwe Kühn, Herbert Kiesele and Stephan Haupt

It is certified that error appears in the above-identified patent and that said Letters Patent is hereby corrected as shown below:

In the title page, in the abstract, line 3: between "including" and "electrode" (first occurrence), insert -- a measuring --.

In column 1, line 12: between "electrodes" and "as", insert -- , --.

In column 1, line 13: between "additive" and "are", insert -- , --.

In column 1, line 34: between "additive" and "but", insert -- , --.

In column 1, line 59: between "surface" and "and", insert -- , --.

In column 1, line 60: between "electrode" and "is", insert -- , --.

In column 2, line 68: delete "HBr," and substitute -- HBr and -- therefor.

UNITED STATES PATENT AND TRADEMARK OFFICE
CERTIFICATE OF CORRECTION

PATENT NO. : 5,316,648

DATED : May 31, 1994

INVENTOR(S) : Uwe Kühn, Herbert Kiesele and Stephan Haupt

It is certified that error appears in the above-identified patent and that said Letters Patent is hereby corrected as shown below:

In column 3, line 12: between "industry" and "as", insert -- , --.

In column 3, line 13: between "industry" and "where", insert -- , --.

In column 3, line 28: between "as" and "additive", insert -- the --.

Signed and Sealed this

Sixteenth Day of August, 1994

Attest:

BRUCE LEHMAN

Attesting Officer     Commissioner of Patents and Trademarks